(12) United States Patent
Lucas et al.

(10) Patent No.: US 6,270,972 B1
(45) Date of Patent: Aug. 7, 2001

(54) KIT FOR DETECTING NUCLEIC ACID SEQUENCES USING COMPETITIVE HYBRIDIZATION PROBES

(75) Inventors: Joe N. Lucas, San Ramon; Tore Straume, Tracy; Kenneth T. Bogen, Walnut Creek, all of CA (US)

(73) Assignee: The Regents of the University of California, Berkeley, CA (US)

( * ) Notice: Subject to any disclaimer, the term of this patent is extended or adjusted under 35 U.S.C. 154(b) by 0 days.

(21) Appl. No.: 09/364,155

(22) Filed: Jul. 30, 1999

Related U.S. Application Data

(63) Continuation of application No. 08/720,540, filed on Sep. 30, 1996, which is a continuation of application No. 08/512,897, filed on Aug. 9, 1995, now Pat. No. 5,616,465.

(51) Int. Cl.[7] ...................................................... C12Q 1/68
(52) U.S. Cl. ............................................. 435/6; 536/24.3
(58) Field of Search .......................... 435/6, 91.2, 91.21; 536/24.3, 24.31, 24.32, 24.33

(56) References Cited

U.S. PATENT DOCUMENTS 4,358,535 11/1982 Falkow et al. ............................ 435/5

(List continued on next page.)

FOREIGN PATENT DOCUMENTS 0 079 139 11/1982 (EP).

(List continued on next page.)

OTHER PUBLICATIONS

Gene Maping and Gene Enrichment by the Avidin–Biotin Interaction: Use of Cytochrome–c as a Polyamine Bridge; Ann Sodja and Norman Davidson; Nucleic Acids Research, vol. 5, No. 2, Feb. 1978, pp. 385–401.

(List continued on next page.)

Primary Examiner—Lisa B. Arthur (74) Attorney, Agent, or Firm—David J. Weitz; Wilson Sonsini Goodrich & Rosati (57) ABSTRACT

A kit is provided for detecting a target nucleic acid sequence in a sample, the kit comprising:

a first hybridization probe which includes a nucleic acid sequence that is sufficiently complementary to selectively hybridize to a first portion of the target sequence, the first hybridization probe including a first complexing agent for forming a binding pair with a second complexing agent; and a second hybridization probe which includes a nucleic acid sequence that is sufficiently complementary to selectively hybridize to a second portion of the target sequence to which the first hybridization probe does not selectively hybridize, the second hybridization probe including a detectable marker;

a third hybridization probe which includes a nucleic acid sequence that is sufficiently complementary to selectively hybridize to a first portion of the target sequence, the third hybridization probe including the same detectable marker as the second hybridization probe; and a fourth hybridization probe which includes a nucleic acid sequence that is sufficiently complementary to selectively hybridize to a second portion of the target sequence to which the third hybridization probe does not selectively hybridize, the fourth hybridization probe including the first complexing agent for forming a binding pair with the second complexing agent;

wherein the first and second hybridization probes are capable of simultaneously hybridizing to the target sequence and the third and fourth hybridization probes are capable of simultaneously hybridizing to the target sequence, the detectable marker is not present on the first or fourth hybridization probes and the first, second, third, and fourth hybridization probes each include a competitive nucleic acid sequence which is sufficiently complementary to a third portion of the target sequence that the competitive sequences of the first, second, third, and fourth hybridization probes compete with each other to hybridize to the third portion of the target sequence.

11 Claims, 3 Drawing Sheets

U.S. PATENT DOCUMENTS

| | | | |
|---|---|---|---|
| 4,376,110 | 3/1983 | David et al. | 435/513 |
| 4,486,539 | 12/1984 | Ranki et al. | 435/504 |
| 4,556,643 | 12/1985 | Paau et al. | 435/501 |
| 4,563,419 | 1/1986 | Ranki et al. | 435/6 |
| 4,775,619 | 10/1988 | Urdea | 435/6 |
| 4,794,082 | 12/1988 | Sigler | 435/177 |
| 5,200,314 | 4/1993 | Urdea | 435/6 |
| 5,273,882 | 12/1993 | Snitman et al. | 435/6 |
| 5,310,650 | 5/1994 | McMahon et al. | 435/6 |
| 5,387,505 | 2/1995 | Wu | 435/6 |
| 5,438,194 | 8/1995 | Koudijs et al. | 435/6 |
| 5,521,300 | 5/1996 | Shah et al. | 435/6 |

FOREIGN PATENT DOCUMENTS

| | | |
|---|---|---|
| 0 285 057 | 6/1983 | (EP). |
| 0 286 898 | 6/1983 | (EP). |
| 0 117 440 | 1/1984 | (EP). |
| 0 231 495 | 12/1986 | (EP). |
| 0 235 726 | 2/1987 | (EP). |
| 0 292 128 | 4/1988 | (EP). |
| WO 83/01459 | 4/1983 | (WO). |
| WO 84/03285 | 8/1984 | (WO). |
| WO 85/04674 | 10/1985 | (WO). |
| WO 87/03622 | 6/1987 | (WO). |
| WO 87/03911 | 7/1987 | (WO). |
| WO 88/01302 | 2/1988 | (WO). |

OTHER PUBLICATIONS

Enzymatic Synthesis of Biotin–labeled Polynucleotides: Novel Nucleic Acid Affinity Probes, Pennina R. Langer, Alex A. Waldrop and David C. Ward; Proc. Natl Acad. Sci. USA, vol. 78, No. 11, pp. 6633–6637 date __.

Ligation of Oligonucleotides to Nucleic Acids or Proteins via Disulfide Bonds, Barbara C. F. Chu and Leslie E. Orgel; Nucleic Acids Research, vol. 16, No. 9, 1988, pp. 3671–3691.

KIT FOR DETECTING NUCLEIC ACID SEQUENCES USING COMPETITIVE HYBRIDIZATION PROBES

RELATIONSHIP TO COPENDING APPLICATIONS

This application is a continuation of application Ser. No. 08/720,540 entitled "KIT FOR DETECTING NUCLEIC ACID SEQUENCES USING COMPETITIVE HYBRIDIZATION PROBES", filed Sept. 30, 1996, now pending which is a continuation of application Ser. No. 08/512,897 entitled "DETECTION AND ISOLATION OF NUCLEIC ACID SEQUENCES USING COMPETITIVE HYBRIDIZATION PROBES", filed Aug. 9, 1995, now U.S. Pat. No. 5,616,465.

The United States government has rights in this invention pursuant to Contract Number W-7405ENG48 between the United States Department of Energy and the University of California for the operation of Lawrence Livermore National Laboratory.

BACKGROUND OF THE INVENTION

1. Field of the Invention

The present invention relates to a method for identifying nucleic acid sequences using two or mere hybridization probes which hybridize to the same nucleic acid sequence.

2. Description of Related Art

A variety of assays have been developed to detect the presence of a particular nucleic acid sequence, hereinafter referred to as a target sequence, through selective hybridization of a hybridization probe to the target sequence. In order for a hybridization probe to hybridize to a target sequence, the hybridization probe must contain a nucleic acid sequence that is at least partially complementary to the target sequence. The complementary sequence of the probe must also be sufficiently long so that the hybridization probe selectively hybridizes to the target sequence over non-target sequences.

In addition to hybridizing a hybridization probe to a target sequence, the hybridization probe must be detectable. A variety of sandwich hybridization assays have been developed which identify a target nucleic acid sequence through the hybridization of a target nucleic acid sequence to two different hybridization probes. The first step of the assay generally involves the hybridization of a target nucleic acid sequence to a first hybridization probe. The hybridized pair is then generally immobilized to a solid support. A second hybridization probe containing a detectable marker is then hybridized to the target sequence, thereby enabling the target sequence hybridized to the first hybridization probe to be detected.

Sandwich hybridization assays require the use of two different hybridization probes where each hybridization probe hybridizes to a separate, non-overlapping portion of the target nucleic acid sequence. However, it is not always possible to design two hybridization probes to a target sequence where each hybridization probe hybridizes to different nonoverapping portions of the target sequence. As a result, some prior art sandwich hybridization assays employ hybridization probes that are not specific for the target nucleic acid. This significantly limits the quantitative accuracy of the assay for detecting target nucleic acid sequences in a sample.

It is an object of the present invention to provide an efficient hybridization assay for the identification of target nucleic acid sequences using two or more hybridization probes which hybridize to the same sequence of a target nucleic acid.

SUMMARY OF THE INVENTION

A method for detecting a target nucleic acid sequence in a sample is provided using two or more hybridization probes which hybridize to the same sequence of a target nucleic acid.

According to an embodiment of the method, a sample containing a target nucleic acid is contacted with a first hybridization probe and a second hybridization probe under conditions favorable for hybridization. The first and second hybridization probes are able to simultaneously hybridize to the target nucleic acid sequence, the first and second hybridization probes including a first fraction of hybridization probes which include a first complexing agent capable of forming a binding pair with a second complexing agent and a second fraction of hybridization probes which include a detectable marker, the second fraction of hybridization probes having the same ratio of first hybridization probes to second hybridization probes as the first fraction.

After the sample containing the target nudeic acid is contacted with the first and second hybridization probes, the first complexing agent attached to the first fraction of hybridization probes is contacted with a second complexing agent, the second complexing agent being attached to a solid support such that when the first and second complexing agents are attached, the target nucleic acids hybridized to the first fraction of hybridization probes become immobilized on to the solid support Once immobilized, the immobilized target nucleic acids are then separated and detected by detecting the detectable marker attached to the second fraction of hybridization probes.

In order to facilitate the detection and quantification of the detectable marker, as well as the isolation of the immobilized target sequences, the first fraction of hybridization probes is preferably detachably linked to the solid support. This may be accomplished by incorporating a detachable linker between the first fraction of hybridization probes and the first complexing agent, between the solid support and the second complexing agent or between the first and second complexing agents. The presence of the released target sequences may be determined by detecting the presence of the detectable marker or by detecting the presence of the released target sequence itself.

When a detachable linker is employed, purification of the target nucleic acid sequence hybridized to the hybridization probes can be accomplished by releasing the target nucleic acid sequences from the solid support, dehybridizing the target sequence from the hybridization probes and isolating the released dehybridized target nucleic acid sequence, for example by gel electrophoresis. Thus, using a detachable linker, the target sequence may readily be isolated and made available for further analysis, such as sequencing.

The first complexing agent is preferably an antigen, antibody, biotin, a biotin derivative or analogue, avidin or an avidin derivative and analogue. The detectable marker is preferably a radioisotope, an isotope measurable by AMS, a fluorescent molecule, a chemiluminescent molecule, an antibody, the nucleic acid itself or an enzymatically modifiable substrate, the modified enzymatic substrate being analytically detectable.

A kit is also provided for detecting a target nudeic acid sequence in a sample. The kit may include a first fraction of hybridization probes having a first hybridization probe and a second hybridization probe, the first and second hybridization probes being able to simultaneously hybridize to the target nucleic acid sequence and a first complexing agent attached to the first and second hybridization probes, the first complexing agent forming a binding pair with a second complexing agent. The kit also includes a second fraction of hybridization probes having the first and second hybridization probes used in the first fraction wherein the ratio of the first to second hybridization probes in the second fraction is approximately equal to the ratio of first to second hybridization probes in the first fraction. The second fraction of hybridization probes also include,s a detectable marker for detecting the target sequence. Optionally, the kit may further include a second complexing agent attached to a solid support as well as instructions for using the kit.

The assay of the present invention may also be readily adapted for the diagnosis of disease, the occurrence of which is associated with and/or identifiable by the presence or absence of a target nucleic acid sequence. According to this embodiment of the invention, the hybridization probe or probes are designed to selectively hybridize to a nudeic acid sequence associated with and/or characteristic of a disease. The present invention also relates to a kit for diagnosing disease using the competitive hybridization assay of t he present invention.

BRIEF DESCRIPTION OF THE DRAWINGS

FIG. 2A illustrates a detectable marker being detected by first digesting the nudeic acids immobilized on the solid support using DNase.

FIG. 2B illustrates the detectable marker being separated from the solid support prior to detection of the detectable marker by the dehybridization of the hybridization probes.

FIG. 2C illustrates the detectable marker being separated from the solid support prior to detection of the detectable marker by detaching the second complexing agent from the solid support.

FIG. 2D illustrates the detectable marker being separated from the solid support prior to detection of the detectable marker by detaching the first and second complexing agents.

FIG. 2E illustrates the detectable marker being separated from the solid support prior to detection of the detectable marker by detaching the first complexing agent from the hybridization probes.

FIG. 2F illustrates the detectable marker being separated from the solid support prior to detection of the detectable marker by detaching the detectable marker from the hybridization probes.

DETAILED DESCRIPTION OF THE INVENTION

The present invention relates to a rapid and efficient hybridization assay for detecting, isolating, and accurately quantifying target nucleic acid sequences in a sample of nucleic acids. According to the method of the present invention, two or more hybridization probes are used which hybridize to the same sequence of a target nucleic acid. By designing the hybridization assay such that only one hybridization site on the target nucleic acid sequence is needed, the need for two separate hybridization probes, as is used in prior art sandwich hybridization assays, is eliminated. This greatly simplifies the complexity of the hybridization assay and makes it possible to assay for any target nucleic acid whose sequence is known.

In a preferred embodiment, the hybridization assay is used to detect the presence or absence of a nucleic acid sequence associated with a disease. For example, the nucleic acid sequence to be detected may be a cancer gene or a pathogen (viral, fungal or bacterial) DNA insert.

According to the assay of the present invention, a sample of nucleic acids is first obtained. In applications where the nudeic acid sample consists of chromosomal DNA, the chromosomal DNA is first isolated from a sample of cells. Chromosomal DNA may be isolated by any of the variety of methods known in the art. For example, the chromosomal DNA may be isolated by the method taught in Vooijs, et al. Am. J. Hum. Genet. 52:586–597 (1993) or by using the GIBCO BRL TRlzol™ Reagent (Life Technologies, Gaithersburg, Md.), each of which is incorporated herein by reference.

Chromosomal DNA may be analyzed as whole chromosomes, chromosome fragments or chromosomal DNA fragments, all of which are hereinafter referred to as chromosomal DNA. The chromosomal DNA may be organized as an extended double strand, as extended nucleosomes, as chromatin fiber, as folded fiber, and as interphase, prophase or metaphase DNA. Sandberg, "The chromosomes in human cancer and leukemia", Elsevier; New York (1980), pp. 69–73.

The hybridization assay of the present invention utilizes the fact that hybridization probes do not perfectly and stoichiometrically hybridize to a target sequence such that only a single hybridization probe binds to a given sequence. Rather, the actual hybridization of a hybridization probe to a target sequence is generally imperfect such that a series of hybridization probes partially hybridize to the same target sequence to which the hybridization probe is complementary. This is particularly true when hybridization probes having a long sequence of nucleic acids are used.

The hybridization assay of the present invention is designed to take advantage of the imperfect, non-stoichiometric hybridization of hybridization probes by utilizing a competitive hybridization scheme in order to detect the presence of a target sequence in a sample of nucleic acids. More specifically, the assay presupposes that the hybridization probes will be imperfect and non-stoichiometric in nature and employs a series of hybridization probes in which the hybridization probes compete to hybridize to the same target sequence.

The competitive nature of the hybridization assay of the present invention provides unusual control over the sensitivity of the hybridization assay. It also provides a faster, more accurate and more sensitive method for detecting and quantifying nucleic acid sequences.

Figure 1:
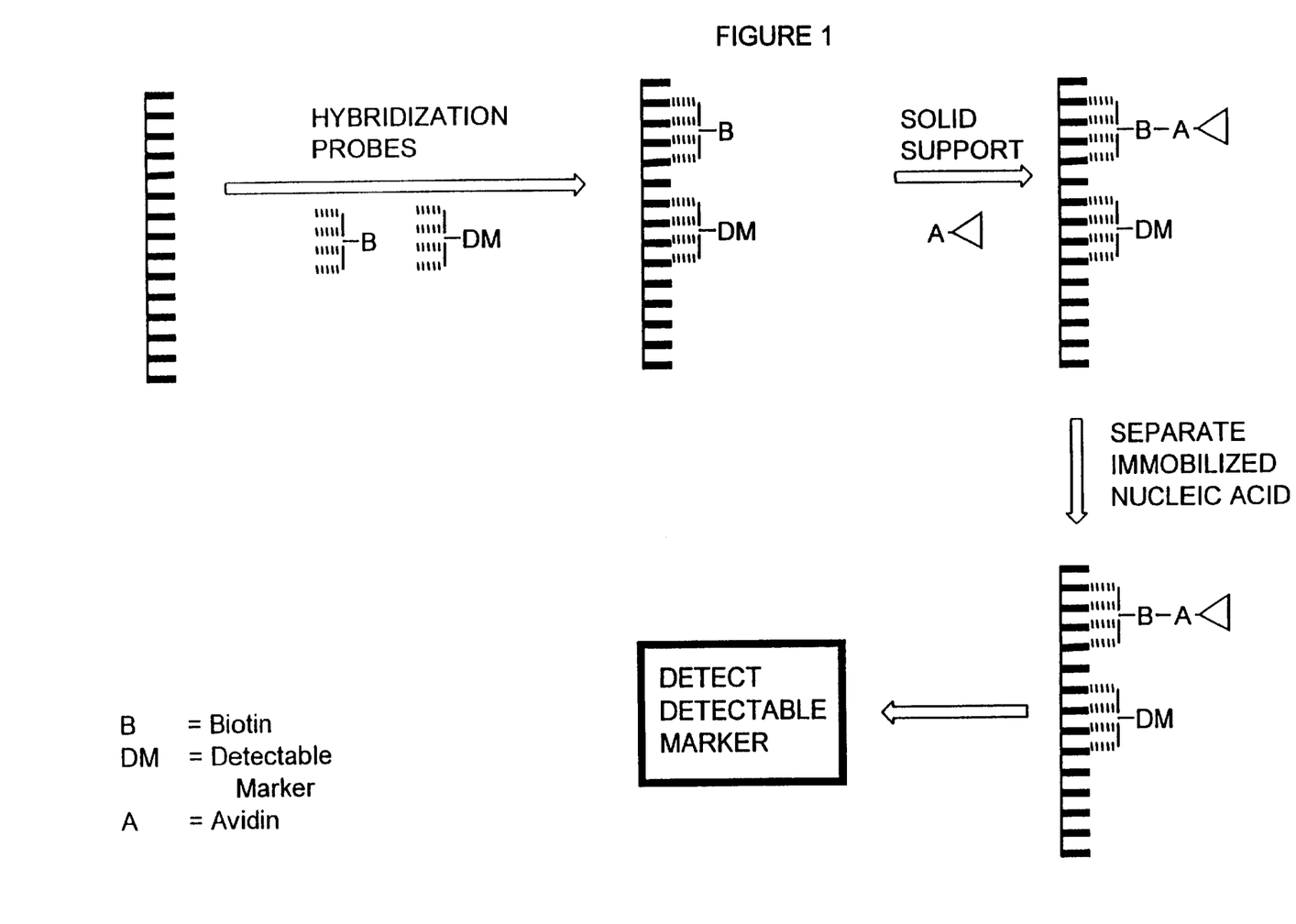
FIG. 1 schematically illustrates the hybridization assay of the present invention using competitive hybridization probes.

The assay is schematically illustrated in FIG. 1. As illustrated in FIG. 1, the sample of nucleic add sequences are simultaneously contacted with a first and a second fraction of hybridization probes under conditions favorable to hybridization. The first fraction of hybridization probes includes a first hybridization probe and a second hybridization probe where the nucleic acid sequences used to form each hybridization probe are able to simultaneously hybridize to the target nucleic add sequence. The first and second hybridization probes may hybridize to separate and distinct portions of the target sequence or, may hybridize to overlapping portions of the target sequence. The first and second hybridization probes are only limited in that the first and second probes each include a nucleic acid sequence that is specific to the target sequence but that does not overlap with the other sequence, thereby enabling both hybridization probes to simultaneously hybridize to the target sequence.

The first and second hybridization probes may include RNA or DNA sequences such that the complementary nucleic acid sequences formed between the hybridization probes and the target sequence may be two DNA sequences, two RNA sequences or an RNA and a DNA sequence.

The hybridization probes in the first fraction further include a first complexing agent capable of forming a binding pair with a second complexing agent which may be attached to a solid support. The formation of a bond between the first and second complexing agent enables the immobilization of the first fraction of hybridization probes to a solid support through the attachment of the second complexing agent to the solid support. In turn, those nucleic acid sequences that hybridize to the immobilized first fraction of hybridization probes will also be immobilized.

The second fraction of hybridization probes includes the same first and second hybridization probes as are employed in the first fraction of hybridization probes except that the hybridization probes in the second fraction include a detectable marker instead of the first complexing agent. As illustrated in FIG. 1, the detectable marker serves to enable the detection of those target sequences that hybridize to at least one hybridization probe from the first and second fractions of hybridization probes.

The ratio of the first hybridization probe relative to the second hybridization probe used in the first fraction of hybridization probes is approximately equal to the ratio of the first hybridization probe relative to the second hybridization probe in the second fraction of hybridization probes. For example, when the ratio of first to second hybridization probe in the first fraction is X:Y, the ratio of first to second hybridization probes in the second fraction also is X:Y. As a result, the first and second fractions of hybridization probes have the same relative concentration of first and second hybridization probes. By keeping the relative concentration of the first hybridization probe to the second hybridization probe constant in both fractions of hybridization probes, the proportion of hybridization probes hybridizing to the target sequence from the first and second fractions should correlate to the ratio of hybridization probes from the first and second fractions that are used.

The ratio between the first and second fractions of hybridization probes may be used to control the sensitivity of the hybridization assay. According to the present invention, the first and second hybridization probes are simultaneously contacted with the sample of nucleic acids such that the two fractions of hybridization probes competitively hybridize to the target sequence. By causing the first and second fractions of hybridization probes to undergo competitive hybridization, and because the first and second hybridization probe fractions contain the same relative concentrations of first and second hybridization probes, the number of first and second hybridization probes that hybridize to the target sequence from each fraction can be controlled as a function of the ratio between the first fraction and the second fraction in the mixture of hybridization probes employed to perform the assay.

The detectable marker is attached to only a given fraction of hybridization probes, i.e., the second fraction of hybridization probes. By using a higher ratio of second fraction probes to first fraction probes, a greater number of second hybridization probes will hybridize to the target sequence. As a result, a greater number of detectable markers will be immobilized to indicate the presence of the target sequence. This enables one to control the amount of detectable marker that becomes attached to the target sequence, thereby providing the user of the present assay with control over the amount of detectable marker that becomes attached to the target sequence. Accordingly, one is able to increase or decrease the sensitivity of the assay of the present invention by increasing or decreasing the ratio of the second fraction of hybridization probes to the first fraction.

It is preferred that the ratio between the first fraction and the second fraction be between about 1:4 and 4:1, more preferably 1:1.

As illustrated in FIG. 1, once the mixture of hybridization probes have been hybridized to the target sequence, the hybridized target nucleic acid sequences are contacted with a second complexing agent bound to a solid support. The second complexing agent forms a binding pair with the first complexing agent which is bound to the hybridization probes of the first fraction. The binding pair formed between the first and second complexing agents serves to immobilize the first fraction of hybridization probes as well as those target sequences which are hybridized to the first fraction of probes. Any hybridization probes from the second fraction which are hybridized to target sequences that are immobilized on the solid support will also become immobilized.

The immobilized target sequences are then separated from any nonimmobilized nucleic acids. Separation of the immobilized nucleic acids from non-immobilized nucleic acids may be accomplished by a variety of methods known in the art including, but not limited to, centrifugation, filtration, magnetic separation, chemical separation and washing.

After the immobilized target sequences have been separated from any non-immobilized nucleic acids, the immobilized sequences are analyzed for the presence of a detectable marker. The quantity of a target sequence in a sample can then be readily determined by quantifying the detectable marker.

The hybridization probes used in the invention are preferably between about 100 and 1000 base pairs long, more preferably between about 200 and 700 base pairs long, and most preferably between about 300 and 500 base pairs long.

The first and second complexing agents used in the embodiment of the present invention may be any pair of complexing agents which form a strong binding pair. Since elevated temperatures are generally required for hybridization, the binding pair should preferably be stable at temperatures at least up to about 37° C. under hybridization conditions.

Examples of suitable binding pairs of complexing agents include antibody-antigen pairs, biotin-avidin and digoxigenin-antidigoxigenin. Avidin-biotin and analogues and derivatives thereof are particularly preferred as binding pairs due to their enhanced thermal stability. Examples of avidin derivatives include, but are not limited to, streptavidin, succinyl avidin, ferritin avidin, enzyme avidin and cross-linked avidin. Examples of biotin derivatives include, but are not limited to caproylamidobiofin and biocytin. Examples of biotin analogues include, but are not limited to desthiobiotin and biotin suffone. Biotin-antibiotin antibody is an example of a suitable antibody-antigen pair.

Any solid support to which a complexing agent may be attached may be used in the present invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Slides can be readily used with any chromosome organization. Due to their flat surface, probe and hybridization reagents can be minimized using glass slides. Slides also enable the targeted application of reagents, are easy to keep at a constant temperature, are easy to wash and facilitate the direct visualization of RNA and/or DNA immobilized on the solid support. Removal of RNA and/or DNA immobilized on the solid support is also facilitated using slides. It is estimated that a standard microscope glass slide can contain 50,000 to 100,000 cells worth of DNA. Beads, such as BioMag Strepavidin magnetic beads are another preferred form of solid support containing a second complexing agent.

It is preferred that avidin or an avidin derivative be used as the second complexing agent. Avidin may be chemically attached to glass using the N-hydroxysuccinamide active ester of avidin as taught by Manning, et al. *Biochemistry* 16:1364–1370 (1977) and may be attached to nylon by a carbodiimide coupling as taught by Jasiewicz, et al. *Exp. Cell Res.* 100:213–217 (1976). Magnetic microbeads labelled with avidin and strepavidin labelled bead may be obtained from Advanced Magnetics, Inc., Cambridge, Mass. and from Spherotech, Inc., Libertyville, Ill.

Any analytically detectable marker that can be attached to or incorporated into a hybridization probe may be used in the present invention. An analytically detectable marker refers to any molecule, moiety or atom which can be analytically detected and quantified. Methods for detecting analytically detectable markers include, but are not limited to, radioactivity, fluorescence, absorbance, mass spectroscopy, EPR, NMR, XRF, luminescence and phosphorescence. For example, any radiolabel which provides an adequate signal and a sufficient half-life may be used as a detectable marker. Commonly used radioisotopes include $^3$H, $^{14}$C $^{32}$P and $^{125}$I. In a preferred embodiment, $^{14}$C is used as the detectable marker and is detected by accelerator mass spectroscopy (AMS). $^{14}$C is preferred because of its exceptionally long half-life and because of the very high sensitivity of AMS for detecting $^{14}$C isotopes. Other isotopes that may be detected using AMS include, but are not limited to, $^3$H, $^{125}$I, $^{41}$Ca, $^{63}$Ni and $^{36}$Cl.

Fluorescent molecules, such as fluorescein and its derivatives, rhodamine and its derivatives, dansyl, umbeliferone and acridimium, and chemiluminescent molecules such as luciferin and 2,3-dihydrophthalazinediones may also be used as detectable markers. Molecules which bind to an analytically detectable marker may also be covalently attached to or incorporated into hybridization probe, for example, as taught by Ward, European Patent Application No. 63,879 which is incorporated herein by reference. In such instances, the hybridization probe is detected by adding an analytically detectable marker which specifically binds to the probe, thereby enabling detection of the probe. Examples of such molecules and their analytically detectable counterparts include biotin and either fluorescent or chemiluminescent avidin. Antibodies that bind to an analytically detectable antigen may also be used as a detectable marker. The detectable marker may also be a molecule which, when subjected to chemical or enzymatic modification, becomes analytically detectable such as those disclosed in Leary, et al., *Proc. Natl. Acad. Sci.(U.S.A.)*. 80:4045–4049 (1983) which is incorporated herein by reference. Other examples of suitable detectable markers include protein binding sequences which can be detected by binding proteins, such as those disclosed in U.S. Pat. No. 4,556,643 which is incorporated herein by reference. As discussed herein, the nucleic acid sequence employed in the first and/or second hybridization probe may function as a detectable marker where the bases forming the nudeic acid sequence are quantified using techniques known in the art.

As discussed herein, the nucleic acid sequence employed in the hybridization probe may itself function as a detectable marker where the bases forming the nucleic acid sequence are quantified using techniques known in the art.

Once any nucleic acids and hybridization probes that are not immobilized to the solid support have been removed, the presence or absence of the detectable marker attached to the second fraction of hybridization probes is detected in order to quantify the target sequence. The detection and quantification of the detectable marker can be performed using a variety of methods, depending upon the particular hybridization probes and detectable markers employed.

In order to facilitate the detection and quantification of the detectable marker, as well as the isolation of the immobilized target sequences, the first fraction of hybridization probes is preferably detachably linked to the solid support. This may be accomplished by incorporating a detachable linker between the first fraction of hybridization probes and the first complexing agent, between the solid support and the second complexing agent or between the first and second complexing agents. The presence of the released target sequences may be determined by detecting the presence of the detectable marker or by detecting the presence of the released target sequence itself.

When a detachable linker is employed, purification of the target nucleic acid sequence hybridized to the hybridization probes can be accomplished by releasing the target nucleic acid sequences from the solid support, dehybridizing the target sequence and the hybridization probes, and purifying the target sequence, for example by gel electrophoresis. Thus, using a detachable linker, the target sequence may readily be isolated and made available for further analysis, such as sequencing.

Figure 2A:
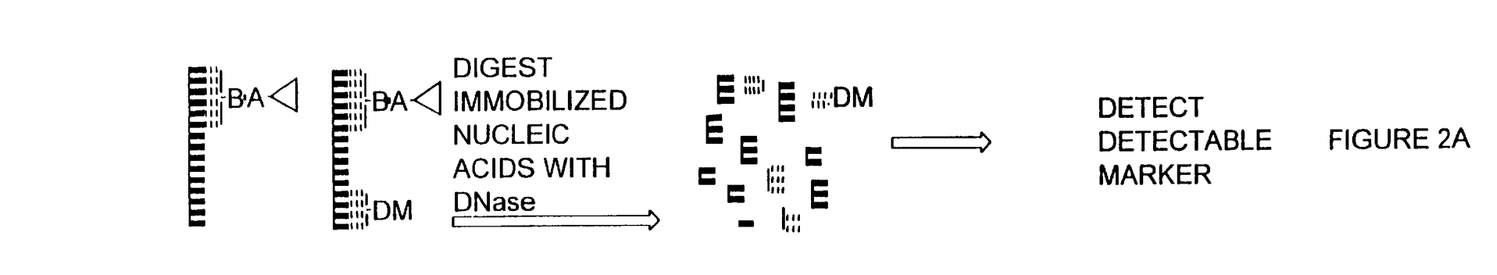
FIGS. 2A–F depict several approaches for isolating and/or detecting the detectable marker on the immobilized hybridization probes where competitive hybridization probes are used.

FIGS. 2A–F illustrate alternate embodiments for detecting the detectable marker. As illustrated in FIG. 2A the detectable marker may be detected by treating the immobilized nucleic acid sequences with DNase to digest any DNA immobilized on the solid support. The digested DNA is then collected after enzymatic digestion and analyzed for the presence of the detectable marker. Alternatively, the nucleic acids attached to the solid support may be removed from the solid support by a variety of chemical and physical methods available, including, for example, treatment with a basic solution (e.g., concentrated NaOH), treatment with an acidic solution and denaturalization of DNA using standard methods such as elevated temperatures or reagents. For example, when the detectable marker used is $^{14}$C, the entire solid support containing the immobilized nucleic acids and hybridization probes may be graphitized and analyzed using accelerator mass spectroscopy (AMS). The use of AMS and a $^{14}$C detectable marker to quantify the target sequence is described in greater detail in Example 1.

Figure 2B:
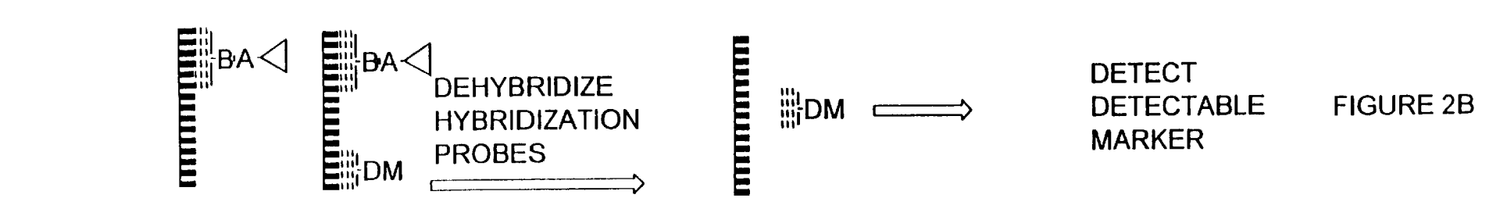

As illustrated in FIG. 2B, the detectable marker may be separated from the solid support prior to detection of the detectable marker by dehybridizing the hybridization probes from the target nucleic acid sequence. This may be done by heating the solid support and immobilized sequences to at least 70° C. in a denaturization solution.

Figure 2C:
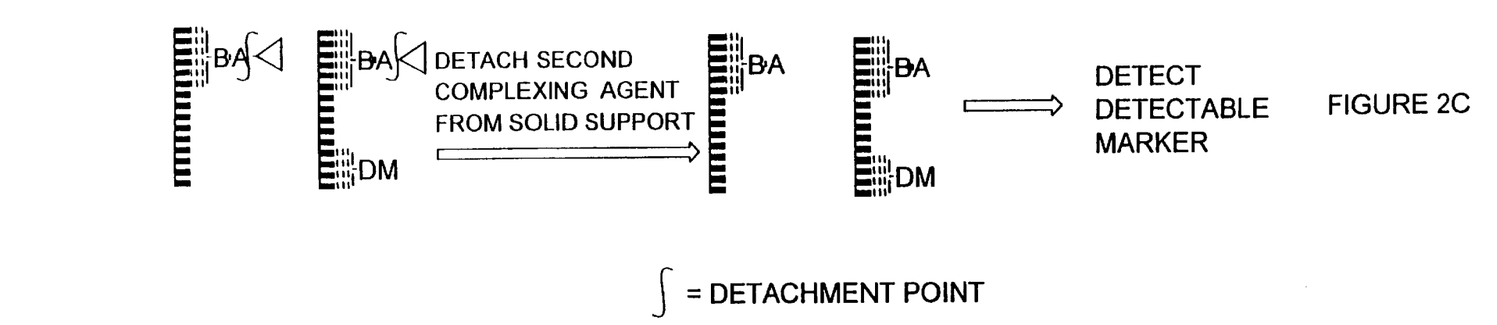

As illustrated in FIG. 2C the detectable marker may be separated from the solid support prior to detection of the detectable marker by breaking the bond between the second complexing agent and the solid support. This may be accomplished through the use of a detachable linker positioned between the second complexing agent and the solid support. Examples of suitable detachable linkages include, but are not limited to the detachable linkers described in Lin, et al., *J. Org. Chem.* 56:6850–6856 (1991); Ph.D. Thesis of W.-C Lin, U. C. Riverside, (1990); Hobart, et al., *J. Immunological Methods* 153: 93–98 (1992); Jayabaskaran, et al., *Preparative Biochemistry* 17 (2): 121–141 (1987); Mouton, et al., *Archives of Biochemistry and Biophysics* 218: 101–108 (1982); Funkakoshi, et al., *J. of Chromatography* 638:21–27 (1993); Gildea, et al., *Tetrahedron Letters* 31: 7095–7098 (1990); WO 85/04674; and Dynabeads (Dynal, Inc., 5 Delaware Drive, Lake Success, N.Y. 11042), each of which are incorporated herein by reference.

Figure 2D:
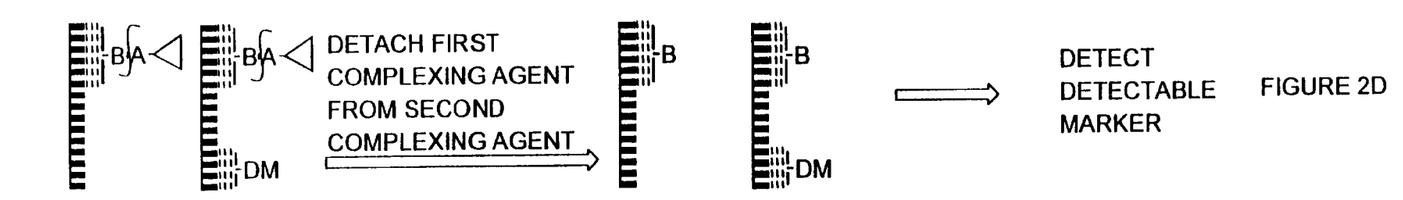

As illustrated in FIG. 2D, the detectable marker may be separated from the solid support prior to detection of the detectable marker by breaking the bond between the first and second complexing agents. For example, using antidigoxigenin and digoxigenin as the first and second binding agents, the bond between the first and second complexing agents may be broken.

Figure 2E:
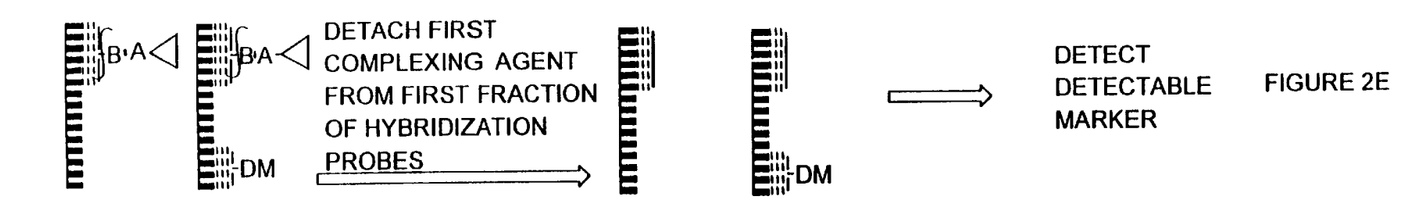

As illustrated in FIG. 2E, the detectable marker may be separated from the solid support prior to detection of the detectable marker by breaking the bond between the first complexing agent and the nucleic acid sequences forming the hybridization probe. This may be accomplished through the use of a detachable linker positioned between the first complexing agent and the nucleic acid sequence forming the hybridization probe. Examples of suitable detachable linkages include, but are not limited to the detachable linkers described in the references cited above.

Figure 2F:
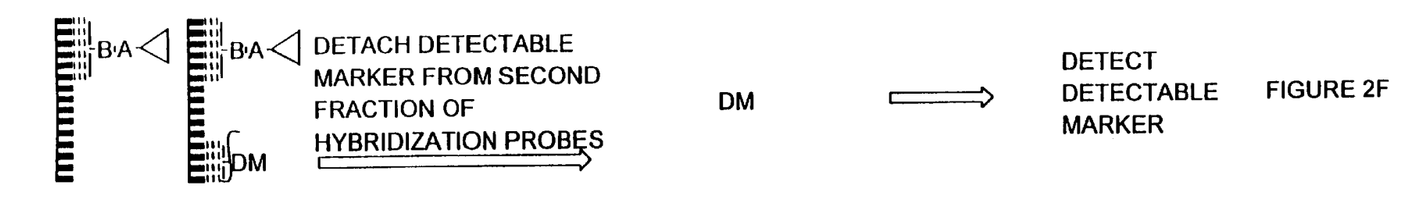

As illustrated in FIG. 2F, the detectable marker may be separated from the solid support prior to detection by detaching the detectable marker from the hybridization probe. This may be accomplished through the use of a detachable linker between the detectable marker and the nucleic acid sequence forming the hybridization probe. Examples of suitable detachable linkages include, but are not limited to, the detachable linkers described in the references cited above.

The detectable marker may be detected by a variety of methods known in the art, depending on the particular detectable marker employed. For example, AMS may be used when the detectable marker is a radioisotope such as $^{14}C$, liquid scintillation may be used when the detectable marker is tritiated thymidine and standard fluorescence or spectroscopic methods may be used when the detectable marker is a fluorescent molecule or the DNA itself.

The quantity of the target nucleic acid sequence that is present may be determined based on the signal generated from the detectable marker using a calibration curve. The calibration curve may be formed by analyzing a serial dilution of a sample of nucleic acids having a known concentration of the target sequence. For example, a calibration curve may be generated by analyzing a series of known amounts of cells from a cell line in which the concentration of the target sequence is known. Alternatively, samples of cells may be analyzed according to the method of the present invention and according to a method known in the art for quantifying the target nucleic acid sequence. Alternative methods for generating a calibration curve are within the level of skill in the art and may be used in conjunction with the method of the present invention.

The present invention also relates to a kit for performing the hybridization assays of the present invention. Unless otherwise specified, the components of the kit are the same as those used in the assays of the present invention.

In one embodiment, the kit includes a first hybridization probe mixture for use as the first fraction in the assay and a second hybridization probe mixture for use as the second fraction in the assay. As specified with regard to the hybridization probe fractions used in the assay, the first and second hybridization probe mixtures each contain the same ratio of first hybridization probes to second hybridization probes. The hybridization probes of the first hybridization probe mixture also include a first complexing agent attached to the probe that is capable of forming a binding pair with a second complexing agent. The hybridization probes of the second hybridization probe mixture include a detectable marker. It is preferred that the detectable marker included on the second hybridization probe mixture be of a known concentration relative to the second hybridization probe mixture. The kit may also include a second complexing agent attached to a solid support capable of binding to the first complexing agent used in first hybridization probe mixture. Optionally, the kit may may also include written instructions for practicing the assay and one or more target nucleic acid sequences for use in the preparation of a calibration curve.

The following examples set forth the method for detecting a nucleic acid sequence according to the present invention. Further objectives and advantages of the present invention other than those set forth above will become apparent from the examples which are not intended to limit the scope of the present invention.

EXAMPLE

Hybridization Assay Employing Competitive Hybridization Probes

A first and a second hybridization probe are generated for a target sequence which can simultaneously hybridize to the target sequence. Several techniques are known in the art for generating single-stranded hybridization probes to a target nudeic acid sequence, for example, as a messenger RNA sequence corresponding to the target sequence, or complementary DNA obtained from reverse transcriptase, or as genomic DNA obtained from the target genome by endonuclease digestion.

Biotinylated first and second hybridization probes are prepared by chemically modifying aliquots of the first and the second hybridization probes to incorporate biotinylated uridine according to the method of Pinkel, et al., *Proc. Natl. Acad. Sci.(USA)* 83:2934–2938 (1986), which is incorporated herein by reference.

$^{14}C$ labelled first and second hybridization probes are also prepared by amplifying the first and the second hybridization probes using pcr in the presence of a $^{14}C$ labelled nudeic add base according to the method described in Vooijs, et al., *Am. J. Hum. Genet.* 52: 586–597 (1993) which is incorporated herein by reference.

The first fraction of hybridization probes is prepared by mixing the first and second biotinylated probes in a 1:1 ratio. The second fraction of hybridization probes is then prepared by mixing the first and second $^{14}C$ labelled probes in a 1:1 ratio. The first and second fractions of hybridization probes are then mixed together such that the ratio between the first and second fractions of hybridization probes is 1:1.

Once the mixture of first and second fractions of hybridization probes has been prepared, the mixture of fractions of hybridization probes are contacted with a sample of nucleic acids under conditions favorable for hybridization.

After hybridization to the sample of nucleic acids has been completed, any unbound probes may optionally be separated from the hybridized target DNA by gel electrophoresis.

The sample of nucleic acids containing the hybridized competitive probes is added to a solid support labelled with avidin to immobilize the first fraction of hybridization probes by an avidin-biofin linkage. Any nucleic acids hybridized to the first fraction of hybridization probes also become immobilized to the solid support. The avidin labelled solid support may be prepared by the methods described in Manning, et al. *Biochemistry* 16:1364–1370 (1977) and Jasiewicz, et al. *Exp. Cell Res.* 100:213–217 (1976), each of which are incorporated herein by reference.

The solid support is then washed with cold, pH 7 buffered saline to remove any first and second hybridization probes and DNA segments which are not immobilized on the solid support.

Once any nonimmobilized nudeic acids have been removed by the saline wash, the remaining immobilized nucleic acids are analyzed for the presence of $^{14}C$. DNase or concentrated NaOH is employed to separate any immobilized nudeic acids from the solid support. The nucleic acids isolated are then grafifized and analyzed using AMS for the presence of $^{14}C$ according to the method of Vogel et. al., *Anal. Chem.* 11: 142–149 (1991) which is incorporated herein by reference.

The $^{14}C$ signal obtained from the accelerator mass spectrometer may be calibrated by performing the assay using a sample containing a known quantity of the target nudeic acid. Alternatively, the nucleic acid sample being analyzed may be analyzed according to the method of the present invention and according to a method known in the art for quantifying the target nucleic acid. Then, by serially diluting the sample of nucleic acids and assaying the sample according to the method described in the present example, a calibration curve may be generated. Alternative methods for generating a calibration curve are within the level of skill in the art and may be used in conjunction with the method of the present invention.

While the present invention is disclosed by reference to the preferred embodiments and example detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A kit for detecting a target nucleic acid sequence in a sample, the kit comprising:
   a first hybridization probe which includes a nucleic acid sequence that is sufficiently complementary to selectively hybridize to a first portion of the target sequence, the first hybridization probe including a first complexing agent for forming a binding pair with a second complexing agent; and
   a second hybridization probe which includes a nucleic acid sequence that is sufficiently complementary to selectively hybridize to a second portion of the target sequence to which the first hybridization probe does not selectively hybridize, the second hybridization probe including a detectable marker;
   a third hybridization probe which includes a nucleic acid sequence that is sufficiently complementary to selectively hybridize to a first portion of the target sequence, the third hybridization probe including the same detectable marker as the second hybridization probe; and
   a fourth hybridization probe which includes a nucleic acid sequence that is sufficiently complementary to selectively hybridize to a second portion of the target sequence to which the third hybridization probe does not selectively hybridize, the fourth hybridization probe including the first complexing agent for forming a binding pair with second complexing agent;
   wherein
   the first and second hybridization probes are capable of simultaneously hybridizing to the target sequence and the third and fourth hybridization probes are capable of simultaneously hybridizing to the target sequence,
   the detectable marker is not present on the first or fourth hybridization probes, and
   the first, second, third, and fourth hybridization probes each include a competitive nucleic acid sequence which is sufficiently complementary to a third portion of the target sequence that the competitive sequences of the first, second, third, and fourth hybridization probes compete with each other to hybridize to the third portion of the target sequence.

2. The kit according to claim 1 wherein the first complexing agent is selected from the group consisting of antigens, antibodies, biotin, biotin analogues, avidin and avidin analogues.

3. The kit according to claim 1 wherein the detectable marker is selected from the group consisting of a radioisotope, a fluorescent molecule, a chemiluminescent molecule, an antibody and an enzymatically modifiable substrate, the modified enzymatic substrate being detectable.

4. The kit according to claim 2 wherein the detectable markers are each independently selected from the group consisting of a radioisotope, a fluorescent molecule, a chemiluminescent molecule, an antibody and an enzymatically modifiable substrate, the modified enzymatic substrate being detectable.

5. The kit according to claim 1 wherein the first, second, third and fourth hybridization probes are each between about 100 and 1000 mucleotides long.

6. The kit according to claim 1 wherein the first, second, third and fourth hybridization probes are each between 200 and 700 mucleotides long.

7. The kit according to claim 1 wherein the first, second, third and fourth probes are each between about 300 and 500 mucleotides long.

8. The kit according to claim 1 wherein the first and second complexing agents are selected such that the attachment between the first and second complexing agents is detachable.

9. The kit according to claim 1 wherein the bond between the first complexing agent and the first hybridization probe is detachable.

10. The kit according to claim 1 wherein the bond between the detectale marker and the second hybridization probe is detachable.

11. A kit according to claim 1 wherein the kit further includes a second complexing agent attached to a solid support.

* * * * *